(12) United States Patent
Witte-Hoffmann

(10) Patent No.: US 9,354,239 B2
(45) Date of Patent: May 31, 2016

(54) BLID; PROTEIN DOMAIN FOR INTERACTION WITH THE BCL-2 FAMILY OF PROTEINS

(71) Applicant: Carlos Witte-Hoffmann, Newburyport, MA (US)

(72) Inventor: Carlos Witte-Hoffmann, Newburyport, MA (US)

( * ) Notice: Subject to any disclaimer, the term of this patent is extended or adjusted under 35 U.S.C. 154(b) by 0 days.

(21) Appl. No.: 14/473,553

(22) Filed: Aug. 29, 2014

(65) Prior Publication Data
US 2015/0233943 A1    Aug. 20, 2015

Related U.S. Application Data

(62) Division of application No. 13/677,280, filed on Nov. 14, 2012, now Pat. No. 8,853,145.

(60) Provisional application No. 61/629,199, filed on Nov. 14, 2011.

(51) Int. Cl.
*C07K 14/475* (2006.01)
*C07K 14/47* (2006.01)
*C12P 21/06* (2006.01)
*G01N 33/68* (2006.01)
*G01N 33/50* (2006.01)

(52) U.S. Cl.
CPC ........ *G01N 33/6872* (2013.01); *C07K 14/4747* (2013.01); *G01N 33/5026* (2013.01); *G01N 2333/4703* (2013.01); *G01N 2500/04* (2013.01); *G01N 2500/10* (2013.01); *G01N 2500/20* (2013.01)

(58) Field of Classification Search
CPC ........... C07K 14/4747; C07K 2319/92; C07K 2319/42; C07K 2319/10
See application file for complete search history.

*Primary Examiner* — Karen Cochrane Carlson

(57) ABSTRACT

In this invention, a novel protein interaction domain is provided along with several of its variants. This domain is involved in protein-protein interactions with the Bcl-2 family of proteins. It is named BLID (Bcl2 family of proteins Like Interaction Domain). Use of BLID and its variants for modulating cellular activity is presented. BLID, its variants and or anti-BLID antibodies could be useful as a screening tool as well as for discovery of drugs that help fight pathological states like degenerative diseases, cerebral or cardiac ischemic hypoxic disorders, cancer and autoimmunity.

9 Claims, 8 Drawing Sheets

E277                    Q333
EGDDQEGEGEKKRKGGRNFQTARNMLKGQHEKEAADRKRKQEEQMETEHQTTCNLQ BLID
      : :.:  ::  :: .  ::  :: .   :  ::     :   :. :
IPMAAVKQALREAGDEFELRYRRAFSDLTSQLHITPGTAYQSFEQVVNELFRDGVN Bcl-XL
I81                                                      N136
      BH3

FIGURE 3

BLID and Bcl-XL/Bim-BH3 complex

BLID and CED-9/EGL-1 complex

FIGURE 8 ptosis.

BLID; PROTEIN DOMAIN FOR INTERACTION WITH THE BCL-2 FAMILY OF PROTEINS

REFERENCE TO RELATED APPLICATION

This application is a Divisional to and claims the benefit of U.S. application Ser. No. 13/677,280 filed by applicant on Nov. 14, 2012; which is related to and claims the benefit of U.S. Provisional Application Ser. No. 61/629,199 filed by applicant on Nov. 14, 2011.

A Sequence Listing is attached to this document.

BACKGROUND OF THE INVENTION

Field of the Invention

This invention relates generally to the fields of molecular biology and molecular medicine and more specifically to proteins involved in the regulation of cellular processes like apoptosis.

Apoptosis is one of the two main types of programmed cell death found during development in a wide spectrum of organisms from *c. elegans* to mammals. Apoptosis is a cellular process common to both physiological and pathological events in cells. Crucial for the execution of apoptosis are two families of proteins: caspases and the Bcl-2 family of proteins (Wyllie, 2010; Conradt, 2009).

The Bcl-2 family of proteins is comprised of two main functional groups: proapoptotic and antiapoptotic. Members of both subgroups interact with each other in a complex network that controls the fate of the cell by triggering or preventing apoptosis.

From the structural point of view, the antiapoptotic group of this family is characterized by having four Bcl-2 Homology (BH) domains. They are called BH1, BH2, BH3 and BH4. The proapoptotic group is further subdivided on a multidomain group; which have BH1, BH2 and BH3 domains and a BH3 only group with only one domain (BH3). The BH3-only group is further functionally subdivided in activators and derepressors, depending on their interactions with either proapoptotic multidomain proteins or with antiapoptotic-proapoptotic protein complexes (Wyllie, 2010; Conradt, 2009).

Representative members of the antiapoptotic group in the Bcl-2 family of proteins are: Bcl-2, Bcl-XL, Mcl-1, Bcl-W, Bfl-1, and Bcl-B. Members of the proapoptotic group of the Bcl-2 family are further subdivided into two groups: Bax, Bak, and Bok (multidomain group) and Bid, Bim, Bad, Puma, Noxa, and others (BH3-only group). These proteins interact with each other in protein-protein interactions mainly through BH domains (Wyllie, 2010; Conradt, 2009).

An imbalance in apoptosis modulation can lead, via either excessive or deficient activity, to pathogenic states like neurodegeneration, heart disease, autoimmunity or cancer respectively (Nemec and Khaled, 2008; Tischner, 2010; Drag and Salvesen, 2010; Volbracht, 2001). Because the Bcl-2 family of proteins plays such an important role in apoptosis its members have been the targets of several approaches of drug discovery efforts. These approaches include small molecule inhibitors, antisense (AS) oligonucleotides, ribozymes, etc. Among the members of the Bcl-2 family currently under investigation are: Bcl-2, Bcl-W, Bcl-XL and Mcl-1 (Ashkenazi and Herbst, 2008; Sasi, 2009).

A salient feature of apoptosis regulation is the redundant role of Bcl-2 family members in these complex networks (Nemec and Khaled, 2008; Sasi, 2009). Finding out how these redundancies occur has been a focus of research as it has a direct impact on therapeutic efforts. One key element of this line of research is identifying new partners and their novel ways of interaction within this complex regulatory network.

We have identified a novel domain involved in apoptosis modulation via its interaction with the Bcl-2 family of proteins. This novel domain was identified in lens epithelium-derived growth factor (LEDGF). BLID and antibodies against it can be used as a screening tool for characterizing the presence and interactions of members the Bcl-2 family of proteins in cells.

We think that several molecules that use this novel domain as a template can be also very useful in drug discovery efforts aimed at fighting disease states like degenerative diseases, cerebral or cardiac ischemic/hypoxic disorders, cancer and autoimmunity.

SUMMARY OF THE INVENTION

In accordance with the present invention, there are provided novel Bcl2 family of proteins Like Interaction Domain (BLID) and several derivative molecules thereof. In addition to these polypeptides, nucleic acid molecules encoding BLIDs, vectors containing these nucleic acid molecules and host cells containing such vectors are indicated. The invention also indicates antibodies that can specifically bind to invention BLIDs. BLID, its derivatives and or anti-BLID antibodies could be useful for screening purposes, for instance in immunoassays aimed at characterizing the presence of BLID itself or Bcl-2 family members in cellular samples.

A very important application of this invention is the use of BLID containing polypeptides and its derivatives in the discovery of drugs that help fight pathological states like cancer, autoimmunity, degenerative diseases, allograph rejection and infection.

The present invention indicates isolation procedures to identify interaction partners for BLID in mammalian cells. Identification of natural BLID partners can be very useful in the study of cell processes like apoptosis. They can be also useful for the design of drugs aimed at modulating programmed cell death in mammalian cells.

The present invention also indicates screening assays useful for identifying agents, which can effectively alter the association of an invention BLID with itself or with other proteins. By altering the self-association of BLID or by altering its interactions with other proteins, an effective agent may increase or decrease BLID action and therefore modulate cellular pathways that effect cellular processes like apoptosis.

The invention also provides methods of altering the activity of BLID in a cell; wherein such increased or decreased activity of BLID can modulate cellular pathways that effect apoptosis. For example, the activity of BLID in a cell can be increased by introducing into the cell a nucleic acid sequence encoding BLID or BLID derivatives and expressing it. Alternatively, BLID and BLID derivatives can be produced via recombinant techniques or chemical synthesis and added to cells to be internalized by the cells. BLID and BLID derivatives can also be microinjected into cells or otherwise introduced into cells in order to modulate cell processes like apoptosis.

BRIEF DESCRIPTION OF THE FIGURES

FIG. 3. Sequence alignment between Bcl-XL and BLID. Sequence alignment between a partial BLID SEQ ID NO: 6 as target and Bcl-XL (PDB 1MAZ) as template in a threading analysis. Aminoacid similarities are indicated as follows: (|): Identical residues, (:): very similar residues (PAM exchange matrix score: 1), (.): weakly similar residues (PAM exchange matrix score: −1). A bar indicates the BH3 motif in Bcl-XL. Critical residues for the BH3 domain are indicated. Residues are color-coded: hydrophobic residues: very light gray; acidic residues: light gray; basic residues: dark gray. Residue positions for Bcl-XL and BLID are indicated.

Figure 8:
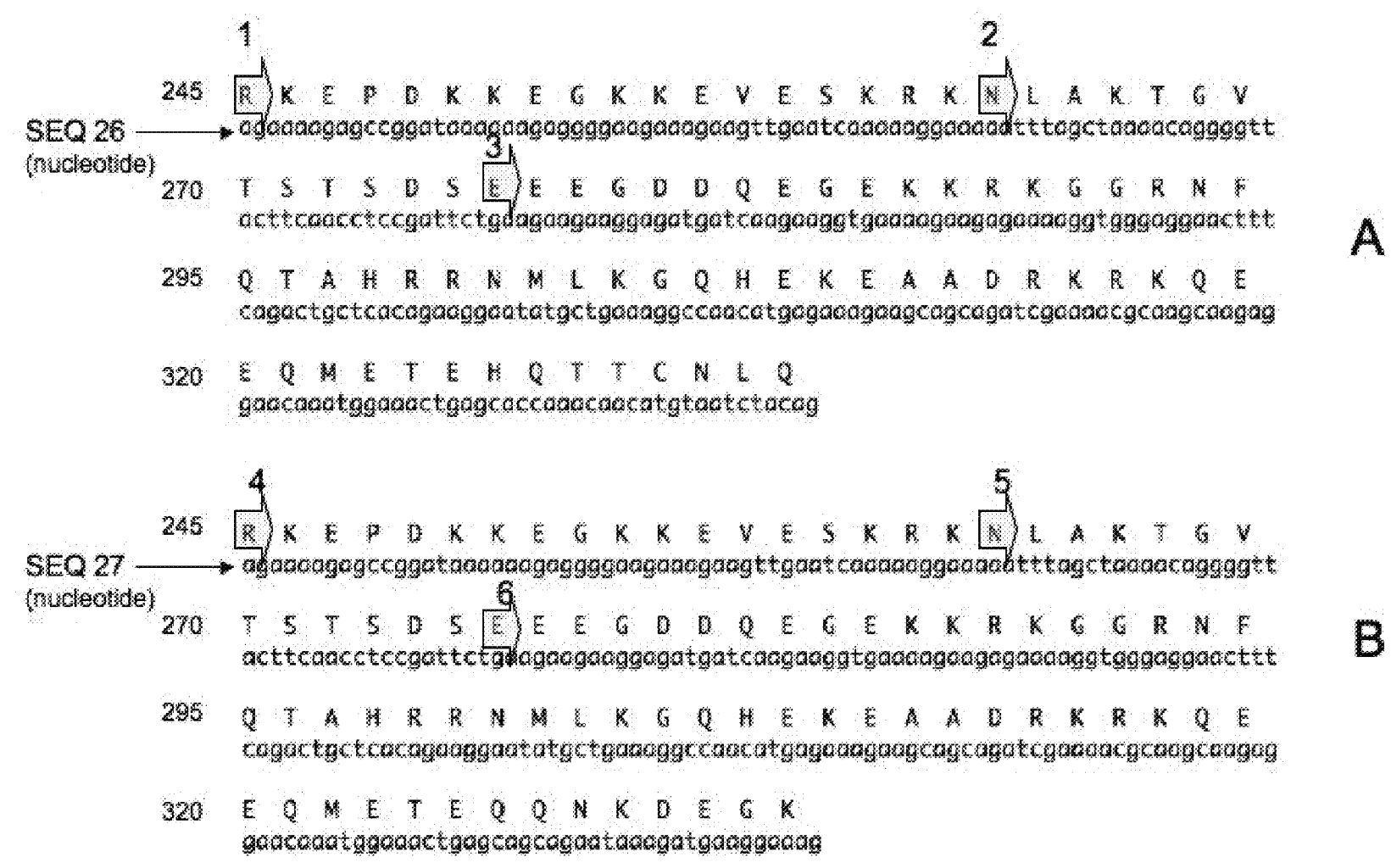

FIG. 8. Examples of BLID protein and nucleotide sequences. A) LEDGF isoform p52 derived sequences. B) LEDGF isoform p75 derived sequences. Examples of BLID polypeptide sequences are indicated: 1 (SEQ ID NO: 1); 2 (SEQ ID NO: 2); 3 (SEQ ID NO: 6); 4 (SEQ ID NO: 12); 5 (SEQ ID NO: 13); 6 (SEQ ID NO: 19). An arrow indicates N-terminal portion of individual polypeptides. Nucleotide sequences are also indicated.

DETAILED DESCRIPTION OF THE INVENTION

Figure 1:
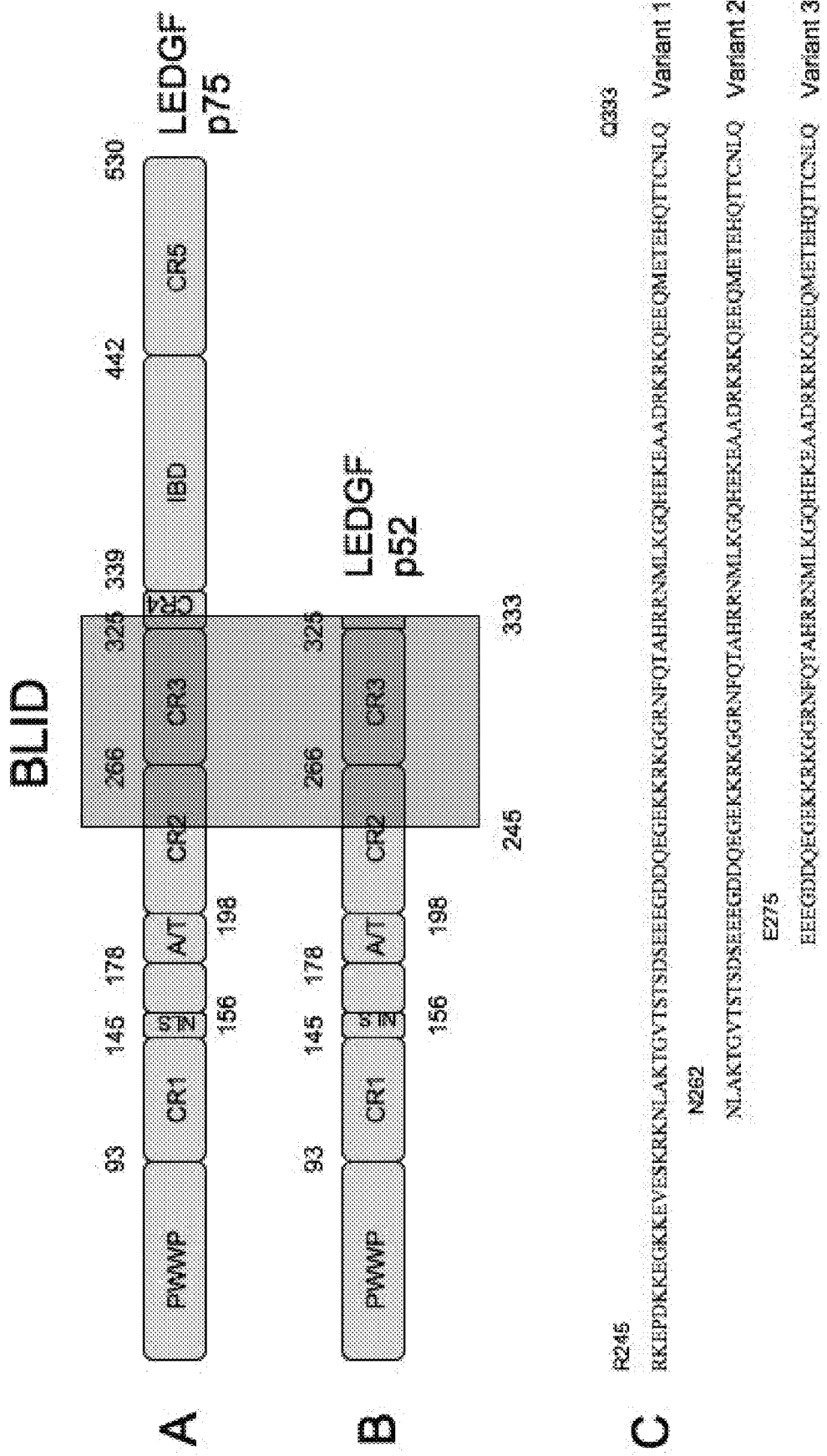
FIG. 1. Definition of the Bcl2 family of proteins Like Interaction Domain on LEDGF. The BLID domain (Bcl-2 family of proteins Like Interaction Domain). LEDGF splice variants A) p75 NM_033222 (NP_150091.2); B) p52 NM_021144 (NP_066967.3). Region boundaries are indicated. PWWP: PWWP domain; CR1-5: Conserved Charged Regions; NLS: Nuclear Localization Signal; A/T: A/T Hooks; IBD: Integrase Binding Domain. The position of BLID on LEDGF is labeled by a square. C) BLID aminoacid sequence, variants 1 (SEQ ID NO: 1), 2 (SEQ ID NO: 2) and 3 (SEQ ID NO: 6), are shown. Residue positions are indicated.

The Bcl-2 family of proteins is comprised of two main functional groups: proapoptotic and antiapoptotic. Members of both subgroups interact with each other in a complex network that controls the fate of the cell by triggering or preventing apoptosis.

From the structural point of view, the antiapoptotic group of this family is characterized by having four Bcl-2 Homology (BH) domains. They are called BH1, BH2, BH3 and BH4. The proapoptotic group is further subdivided into a multidomain group; which has BH1, BH2 and BH3 and a BH3 only group with only one domain (BH3). The BH3-only group is further functionally subdivided in activators and de-repressors depending on their interactions with either proapoptotic multidomain proteins or with antiapoptotic-proapoptotic protein complexes (Drag and Salvesen, 2010; Conradt, 2009; Wyllie, 2010)

Representative members of the antiapoptotic group in the Bcl-2 family of proteins are: Bcl-2, Bcl-XL, Mcl-1, Bcl-W, Bfl-1, and Bcl-B. Members of the proapoptotic group of the Bcl-2 family are further subdivided into two groups: Bax, Bak, and Bok (multidomain group) and Bid, Bim, Bad, Puma, Noxa, and others (BH3-only group). These proteins interact with each other in protein-protein interactions mainly through BH domains. (Drag and Salvesen, 2010; Conradt, 2009; Wyllie, 2010)

An imbalance in apoptosis modulation can lead, via either excessive or deficient activity to pathogenic states like neurodegeneration, heart disease, autoimmunity or cancer respectively (Nemec and Khaled, 2008; Tischner, 2010; Drag and Salvesen, 2010; Volbracht, 2001). Because the Bcl-2 family of proteins plays such an important role in apoptosis its members have been the targets of several approaches of drug discovery efforts. These approaches include using peptides, small molecule inhibitors, antisense (AS) oligonucleotides, ribozymes, etc. Among the members of the Bcl-2 family currently been investigated are: Bcl-2, Bcl-W, Bcl-XL and Mcl-1 (Ashkenazi and Herbst, 2008; Sasi, 2009; Leibowitz and Yu, 2010).

One of the fundamental traits of cancer cells is their resistance to apoptosis. As a result a great deal of research has been devoted to overcome this resistance and use the pre-existing apoptotic machinery against tumor cells (Sasi, 2009; Leibowitz and Yu, 2010).

The more advanced drug against a Bcl-2 protein family member is Oblimersen (an antisense agent against Bcl-2) currently in clinical trials phase III. The success of this drug has been uneven with positive results in some tumors types like chronic lymphocytic leukemia and melanoma and disappointing results in others like prostate, myeloma, and acute myeloid leukemia. (Ashkenazi and Herbst, 2008). Another antisense drug is AS Bcl-2 (G3139) (Sasi, 2009).

Another approach to drug discovery is based on small molecules acting as inhibitors of anti-apoptotic members of the Bcl-2 family of proteins. These compounds are commonly known as BH3 mimetics. An example of these compounds is ABT-263, a small molecule that binds in the sub-nanomolar range to Bcl-2, Bcl-XL, and Bcl-W. GX-15-070 (obatoclax) is another inhibitor of 5 members of the Bcl-2 family of proteins, which is in phase II of clinical trials. In addition, antagonists of Mcl-1 are being developed (Ashkenazi and Herbst, 2008). Other examples are ABT-737 (a Bcl-2 XI antagonist) and WL-276. Another group of small molecule Bcl-2 inhibitors are (−)-Gossypol (AT-101) and a less toxic derivative labeled apogossypol (NSC736630) (Sasi, 2009; Akiyama, 2009). AT-101 is currently in phase I of clinical trials (Ashkenazi and Herbst, 2008).

At the post-transcriptional level Bcl-2 has been targeted with ribozymes (Sasi, 2009). Bim has been the target in studies using siRNA in the context of fighting sepsis in a murine model (Hattori, 2010).

It is also important to note that modulation over Bcl-2 can affect programmed necrosis also and as such be a promising candidate for clinical programmed necrotic cancer therapy (Sasi, 2009).

After filing our initial application we found out that a protein reported as BRCC2 (breast cancer cell 2) (Kasid 2003; Broustas 2004; Lomonosova 2008) had its name changed to BLID (BH3-like motif containing, cell death inducer) (Broustas 2010). This protein is related to Bad, Puma etc both functionally (proapoptotic) and structurally (single BH3 motif); but it has a variation on its BH3 motif (it has no aspartate) and therefore is classified as BH3-Like. It should be noted that the name we used stands for a different acronym (Bcl2 family of proteins Like Interaction Domain) it is derived from a different protein (LEDGF) and it is a domain.

PC4- and SF2-interacting protein 1 (Psip1) is encoded by the PSIP1 gene. This gene encodes two isoforms, p75 (530 aa) and p52 (333 aa). These two proteins share the first 325 N-terminal residues. The most commonly used name for this protein is lens epithelium-derived growth factor (LEDGF), it is also known as dense fine speckles 70 kDa autoantigen or DSF70 (Sutherland, 2006; Hendrix, 2010; Sugiura, 2007).

LEDGF was initially isolated and characterized as a transcriptional co-activator (Ge, 1998). An independent group determined its role as a survival factor in lens epithelial cells under different environmental stresses (Singh, 1999). LEDGF has been proposed as a transcriptional regulator of several stress-related genes (Matsui, 2001). The antiapoptotic effect of LEDGF is believed to occur via transcriptional activation of stress related genes (Sutherland, 2006).

This protein is also an autoantigen found in patients with atopic dermatitis and other inflammatory disorders involving an imbalance of apoptosis regulation. LEDGF is also cleaved by caspases during apoptosis (Sutherland, 2006). The p75 isoform of LEDGF co-precipitates with integrase (IN) from human immunodeficiency virus type 1 (HIV-1). This discovery brought a lot of attention to this protein; suggesting a role in integration of the HIV (Cherepanov, 2003). In addition LEDGF has been connected with oncogenesis (Hendrix, 2010). This protein has been covered in several US patents (Shinohara, et al U.S. Pat. No. 6,750,052; Debyser, et al U.S. Pat. No. 7,514,233 and U.S. Pat. No. 8,008,470; Goldstein, et al. U.S. Pat. No. 8,168,393)

Several domains have been identified in LEDGF. The N-terminal PWWP domain, (residues 1-93) belongs to the family of Tudor domains involved in chromatin binding (Hendrix, 2010; Shun, 2008). The PWWP domain includes a Pro-Trp-Trp-Pro motif, and it has been identified in about 60 eukaryotic proteins. The next domain is CR1 (residues 94-142); one of several conserved charged regions (CR) found in LEDGF. These regions contain a high concentration of positively charged residues and are thought to be involved in electrostatics interactions with DNA chromatin (Hendrix, 2010; Botbol, 2008). A nuclear localization domain (NLS) is found between residues 146-156. This domain is mainly connected to the nuclear localization of this protein as well as contributing to chromatin binding (Meehan, 2009; Botbol, 2008). A A-T Hooks domain (residues 178-198) contains two motifs, that along with the NLS form a tripartite element that cooperates with the PWWP domain in chromatin binding (Garcia-Rivera, 2010; Hendrix, 2010; Botbol, 2008).

Regions CR2 (residues 199-266), CR3 (residues 267-325) and CR4 (residues 326-339) have similar properties to CR1. These are thought to be involved in nonspecific electrostatic interactions with chromatin DNA. Segments of CR2 have high contents of lysines, which are proposed to be targets for posttranslational modifications like SUMOylation, ubiquitination, and glycosylation. (Garcia-Rivera, 2010; Meehan, 2009; Hendrix, 2010). A stretch of serines (S271, S273 and S275) in CR3 has been identified as having phosphorylated Ser/Thr sites and it has been proposed to be a target for protein kinase casein kinase 2 (PKCK2) (Garcia-Rivera, 2010). CR2 and CR3, with no autonomous chromatin binding activity appear to enhance the activity of the N-terminal domains specifically involved in chromatin binding. (Llano, 2006; Meehan, 2009).

The Integrase Binding Domain (IBD) (residues, 347-429) (Meehan, 2009; Hendrix, 2010; Shun, 2008; Botbol, 2008) is involved in protein-protein interactions with the Integrase (IN) from human immunodeficiency virus type 1 (HIV-1). The region CR5 (residues 443-530) located C-terminal from IBD, does not have a high concentration of charge residues but it is conserved. CR5 also contains four demonstrated Ser/Thr phosphosites, three of them clustered near the C-terminal end (Garcia-Rivera, 2010).

The term "functional equivalent", when used herein as a modifier of invention BLID, or polypeptide fragment thereof, refers to a polypeptide that exhibits functional characteristics similar to a BLID. For example, one biological activity or function of BLID is the ability to bind, preferably in vivo but also in vitro, to a member of the Bcl-2 family of proteins, like Bid or Noxa.

Preferably, a "functional equivalent" may be a polypeptide and its encoding nucleic acid that displays substantially similar activity compared with BLID or fragments thereof in a suitable assay for the measurement of biological activity or function. For instance a functional equivalent could display between 20-40%, 40-50%, 60-70%, 70-80%, 80-90% or even more than 100% activity in comparison with BLID in cell survival assays.

Also a "functional equivalent" may be a polypeptide able to function in a similar fashion; both in vivo or in vitro; when compared with the invention BLID and fragments thereof. In an in vitro example, a peptide derived from a BLID sequence is used either in its original composition or further chemically modified (for instance with the substitution of a residue with an amino acid derivatives like 3,4-dihydroxy-phenylalanine, cyclohexyl-glycine, etc or alternative amino acids like D-Ala). This functional equivalent peptide is used to disrupt the binding between an antibody raised against BLID and fragments thereof in an immuno assay, like an ELISA. The reduced binding activity will diminish by at least 10%, more preferably between about 10% and 35%, even more preferably between about 35% and 45%, and most preferably between about 45% and 50%.

When referring to a polypeptide which exhibits "significant structural homology" to polypeptides described in this invention (BLID) we mean polypeptides that while having low sequence identity as compared to the BLID polypeptides, are predicted to be related molecules by virtue of sharing significant structural homology with the BLID polypeptide sequences. The structural homology can be calculated using different structural genomics computational methods for structure analysis, using comparison between experimental structures and or models. As experimental BLID structures become available other software like Probability of Identity 2 (PRIDE2) (Vlahovicek et al 2005) can be used. For instance it can be considered that a polypeptide has a significant structural homology to BLID if it has a PRIDE2 score between 0.6 and 0.8; preferably a PRIDE2 score >0.85 and even more preferably a PRIDE2 score >0.9.

We have identified the BLID domain to have a similar topology to a region of Bcl-XL and Bcl-W and CED-9, three members of the Bcl-2 family of proteins. Bcl-2 family of proteins generally are known to interact with several members of both proapoptotic and antiapoptotic members of said family of proteins, such as Bcl-2, Bcl-XL, Mcl-1, Bcl-W, Bfl-1, Bcl-B, Bax, Bak, Bok, Bid, Bim, Bad, Puma, Noxa, and others.

We hypothesized that, despite a low sequence similarity between a portion of LEDGF and the Bcl-2 family of protein members, they shared a common overall fold. Conservation of protein structure has been found to be stronger than protein sequence during evolution (Graham et al 2008). Recent discoveries of viral proteins with very little sequence identity (less than 15%), but a similar protein fold and function to members of the Bcl-2 family of proteins illustrates this point (Cooray, 2007; Aoyagi, 2007; Kvansakul, 2008 and Douglas, 2007). Such common fold would in turn suggest a similar function and therefore indicate the presence of a novel domain in LEDGF. The presence of such domain would have direct implications on the biological role of LEDGF as well as constituting a new avenue for modulation of cellular processes such as apoptosis.

The divergence of residue types observed between N1L and Bcl-XL in the interaction with a Bim-BH3 peptide indicates the flexibility of arrangement possible for the same type of biologically meaningful interaction, for instance the presence of charged residues in N1L (D35; R71) instead of hydrophobic ones in Bcl-XL (Y101; A142) (Cooray 2007). This flexibility is also observed for BLID, suggesting a possible role in similar interactions with a similar peptide motif from a member of the Bcl-2 family of proteins.

Finding similar results in homology modelling exercises using three members of the Bcl-2 family of proteins (Bcl-XL, Bcl-w and the Bcl-2 *c. elegans* homologue CED-9) and BLID strengthens the case for the presence of a partial structural homolog in this newly defined LEDGF domain.

It is important to note that BLID fold similarities have been calculated with anti-apoptotic members of the Bcl-2 family of proteins, which suggests a similar activity that is an anti-apoptotic activity, for BLID. This anti-apoptotic role for BLID suggests that the more likely interaction partners for this polypeptide are the pro-apoptotic members of the Bcl-2 family of proteins (like Bim, Bid, Noxa, Puma, Bax etc) or with yet unknown proteins with a similar pro-apoptotic role.

All of the above analysis suggests that there is a domain in LEDGF with a similar fold to members of the Bcl-2 family of proteins. This domain can be involved in a new type of protein-protein interaction with members of the Bcl-2 family of proteins. This constitutes a novel interaction for LEDGF, which previously has been regarded as a transcriptional co-activator.

Because of the above mentioned potential novel interactions, BLID and its derivatives can be used as a way of modulating cell physiology; mainly apoptosis but also autophagy and necrosis. Molecules that disrupt the interactions between BLID, its derivatives and their cellular interacting partners can also be used for therapeutic or diagnostic means. As a result, this invention can open new avenues in the fight against disease states like degenerative diseases, stroke, autoimmunity and cancer.

Polypeptides containing BLID and its variations can be expressed and purified using known recombinant techniques (Sambrook, 1989). These BLID containing polypeptides can also be fused to other polypeptides to enhance solubility, provide structural stability, direct cellular localization, facilitate uptake by the cell, facilitate purification, act as a tag for detection etc. Among these fused polypeptides (but not limited to) are GST (Glutathione-S-Transferase), MBP (Maltose Binding Protein), His-Tag, an antibody, HA-Tag, EGFP, Inteins, Streptavidin, TAT (HIV derived cell penetrating peptide) etc.

Nucleotide sequences are also provided which code for the polypeptides defined for BLID and its variants, SEQ ID NO: 26 and SEQ ID NO: 27 code for the longest variants (variants 1 (SEQ ID NO: 1) and 4 (SEQ ID NO: 12) respectively. The nucleotide sequence for the shorter sequences can be assigned from the corresponding polypeptide sequences already defined and from FIG. 8. These nucleotide sequences are used for designing primers for PCR as well as guides for other recombinant technology procedures like cloning, hybridizations, expression etc. These nucleotide sequences are also useful as templates to design probes used for isolating other similar sequences from genetic libraries.

BLID containing molecules can be used to isolate interacting partners using common assays for studying protein-protein interactions. Non-limiting examples of these are: protein complexes isolation via affinity chromatography, affinity tags (like GST or MBP) or Immunoprecipitation. Biochemical methods for protein complexes purification like FLAG-tagged affinity purification or tandem affinity procedure (TAP) can also be employed to isolate BLID partners. The resulting enriched protein fractions are subjected to Isoelectric Focusing Electrophoresis (IEF) and or SDS-PAGE Electrophoresis. Two dimensional-differential gel electrophoresis (2D-DIGE) can also be employed. Specific bands or spots are then analyzed by matrix assisted laser desorption ionization time of flight mass spectrometry (MALDI-TOF MS). Afterwards, the obtained sequences are compared against non-redundant protein databases like NCBI non-redundant protein sequence database. Additional techniques like phage display and protein microarray technology can also be useful to identify BLID partners. Genetic based strategies like yeast two hybrid and its mammalian counterparts can be used to isolate BLID partners as well.

Once BLID containing molecules interaction partners have been isolated, a number of drug discovery efforts can be designed around the BLID containing molecules-partner interactions. Efforts would be directed to either disrupt or promote said interactions. Non-limiting examples of these drug discovery efforts are the use of combinatorial chemical libraries, combinatorial peptide libraries, antisense and Interfering RNA (siRNA, shRNA etc) techniques and structure-based computer screening for binding sites similarities.

The invention will now be described in greater detail by reference to the following non-limiting examples.

EXAMPLES

Example 1

Definition of the Bcl2 Family of Proteins Like Interaction Domain on LEDGF

We called this domain BLID (Bcl2 family of proteins Like Interaction Domain). The overall position of BLID within LEDGF and the aminoacidic sequence of three BLID variants modelled after LEDGF/p52 are shown in FIG. 1. BLID variants 4 (SEQ ID NO: 12), 5 (SEQ ID NO: 13) and 6 (SEQ ID NO: 19) are modelled after LEDGF/p75; they have the same N-terminal position as variants 1 (SEQ ID NO: 1), 2 (SEQ ID NO: 2) and 3 (SEQ ID NO: 6) respectively but differ in their last 8 C-terminal residues. All BLID sequences are shown in the sequence list.

We analyzed BLID for secondary structure. Two different secondary prediction algorithms were applied: Chou-Fasman and Garnier-Robson, using the program Protean 3.02 (DNAStar software suite). We also used data from the crystal structures of a member of the Bcl-2 family of proteins, Bcl-XL and N1L. N1L is a Vaccinia virus protein, which shares fold and function with Bcl-XL and other members of the Bcl-2 family of proteins despite a very low sequence identity (Cooray, 2007; Aoyagi, 2007).

Figure 2:
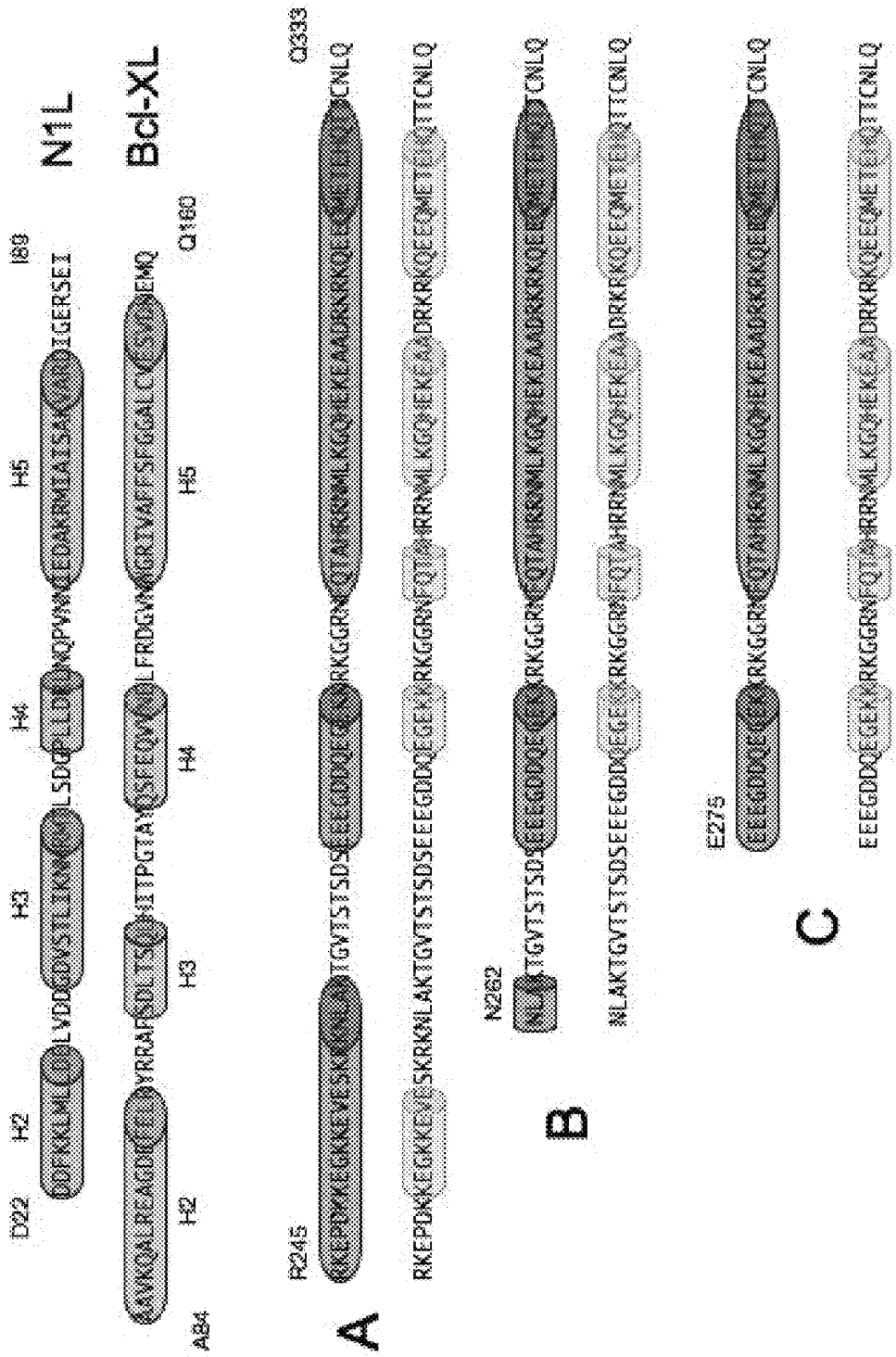
FIG. 2. BLID secondary structure prediction. Top panel: Position of α-helices (cylinders) from the structures of N1L (PDB 2UXE) and Bcl-XL (PDB 1MAZ) are shown (helices 2-5). Bottom panel: Secondary structure predictions for BLID based on two different prediction algorithms, dark gray: Garnier-Robson algorithm (top sequence) and light gray: Chou-Fasman algorithm (bottom sequence). A, B and C represent BLID variants 1 (SEQ ID NO: 1), 2 (SEQ ID NO: 2) and 3 (SEQ ID NO: 6) respectively. Residue positions for N1L, Bcl-XL and LEDGF are indicated.

FIG. 2 shows the resulting secondary structure predictions mapped onto the primary sequence of LEDGF and compared with known structural elements found in N1L and Bcl-XL. The analysis predicts a similar array of multiple helices for BLID when compared with Bcl-XL and N1L. Some of the predicted helices for BLID are in similar positions to helices found in N1L and Bcl-XL.

FIG. 3 shows the results of an alignment between Bcl-XL and BLID variant 3 from a homology modelling test (manual mode) done with Swiss-PdbViewer 4.01 (OS X). The target sequence used was BLID variant 3 and the template used was the crystal structure of Bcl-XL (pdb code 1MAZ). The resulting provisional 3D structure shows several residues corresponding to helices 2-4 of Bcl-XL are found with several degrees of conservation in BLID. The threading energy calculated for this arrangement was −1.2.

An arrangement of residues similar to the BH3 motif in Bcl-XL is found in a segment of BLID (F293-L302). This segment is located near the BH3 region of Bcl-XL. In addition, this region contains a cluster of identical residues between the two polypeptides. This data suggests the presence of a similar BH3 motif in BLID.

BH3 domains have been difficult to identify from sequence alone because the pattern of residues is poorly conserved and there are no invariant residues. In order to identify these domains a combination of sequence and structural analyses, as well as a common molecular mechanism for binding to other Bcl-2 family of proteins may be necessary (Sinha 2008).

Figure 4:
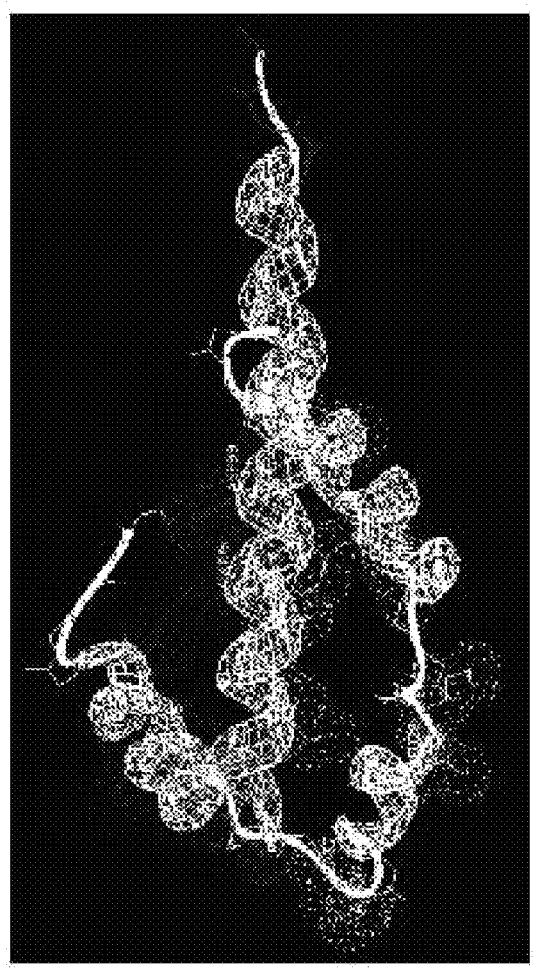
FIG. 4. Threading analysis of BLID. A Bcl-XL complex with Bim-BH3 peptide (PDB 1PQ1) and Bcl-W (PDB 1OOL) were used as templates and BLID SEQ ID NO: 6 was used as a target. A) Frontal view of a provisional 3D structure shows BLID helices in relationship with the Bim BH3 peptide. B) Side view of A. Threading energy was −2.4. Residues forming the BH3 motif on Bim and proposed interacting residues on BLID have their residue position labeled and their contact surfaces (Van der Waals radius) are represented by dots. On Panel A individual helices can be identified, from right to left, helix 2 coming down on a 45 degree angle, followed by helix 3 and finally helix 4 coming up in a 45 degree angle, the helix corresponding to Bim-BH3 is seen in an horizontal orientation.
Figure 4:
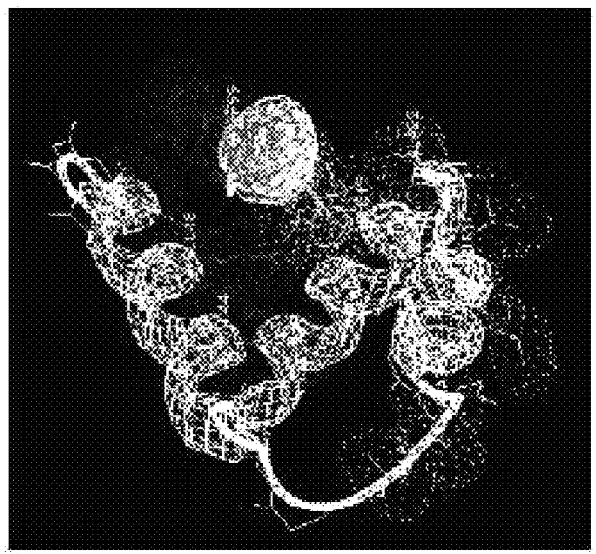

FIG. 4 shows the basic structural elements of BLID. These elements are represented on a provisional 3D structure obtained in a manual mode homology modelling test done with Swiss-PdbViewer 4.01 (OS X). A structure of Bcl-XL in complex with a peptide containing the BH3 motif of Bim (PDB 1PQ1) was superimposed with a Bcl-w (PDB 1O0L) structure and then both were used as template with BLID SEQ ID NO: 6 primary sequence as target in a threading analysis. The threading energy calculated for this arrangement was −2.4.

Several residues in BLID are in position to accommodate the amphipathic nature of the incoming BH3-peptide from Bim. In a front view (panel A) several hydrophobic residues are found in BLID proposed helices 2 and 3 and in the loops among helices 2-4. These hydrophobic residues are facing the hydrophobic face of the BH3 helix. It appears as if the BH3 peptide is in the process of advancing in the frame created by BLID's three proposed helices.

As shown in Panel A, F19 and A22 from BLID are involved in the initial interaction with L94 and F101 from Bim-BH3. Further positioning of the BH3 peptide into BLID's frame (moving to the left on Panel A) will engage a third hydrophobic residue (L90) with the hydrophobic part of BLID's frame.

BLID residues are distributed in two distinct sections along its frame. The first is a hydrophobic sector composed of F19, A22, M27, L28, A36 and A37, which stretches from the C-terminal portion of the proposed helix 2 to the loop between helix 3 and 4. The second section is a charged sector composed of E44, E48 and H51 on helix 4. These two sections are position facing the hydrophobic and charged faces of the incoming BH3 peptide as shown in a side view (panel B). If the BH3 peptide is moved further to the left in Panel A, it will come into contact with more matching elements of BLID's frame in a similar fashion as the interaction described with other Bcl-2 family of protein members.

The divergence of residue types observed between N1L and Bcl-XL in the interaction with a Bim-BH3 peptide indicates the flexibility of arrangement possible for the same type of biologically meaningful interaction, for instance the presence of charged residues in N1L (D35; R71) instead of hydrophobic ones in Bcl-XL (Y101; A142) (Cooray 2007). This flexibility is also observed for BLID, suggesting a possible role in similar interactions with a similar peptide motif to a member of the Bcl-2 family of proteins. Additional threading analysis of BLID variants suggests variants 1-3 are more effective in adopting the proposed fold.

Figure 6:
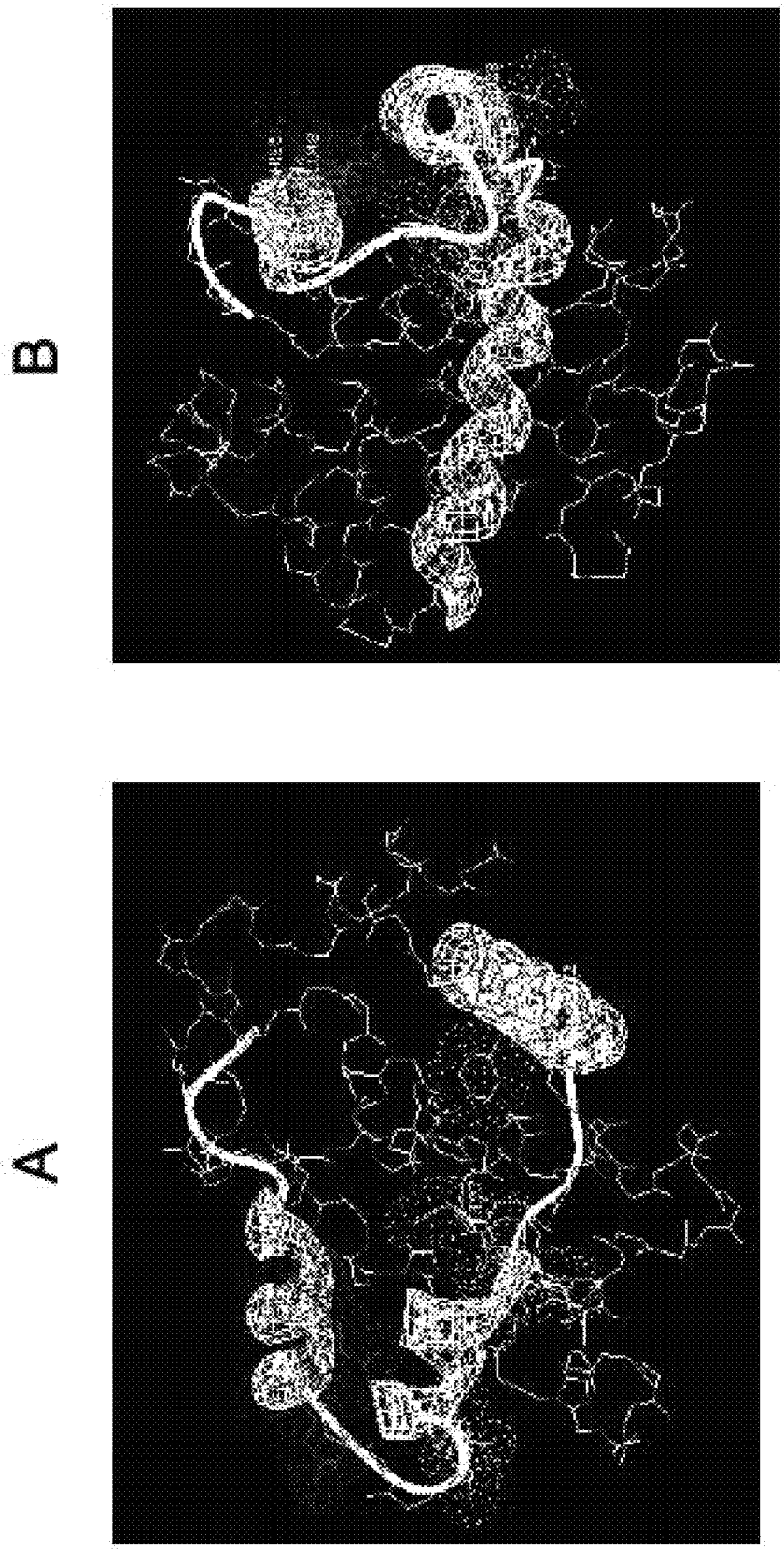
FIG. 6. Another example of a BLID model. BLID SEQ ID NO: 2 was used as a target and the crystal structure of Bcl-XL (PDB 1 PQ0) as template in a threading analysis. Threading energy was −3.8. A) Frontal view with modeled helices for BLID. B) Side view of A. Proposed interacting residues on BLID have their residue position labeled and their contact surfaces (Van der Waals radius) are represented by dots. On Panel A individual helices can be identified, from right to left, helix 2 is the first one coming down and out of the figure, to the left helix 3 is at the bottom and helix 4 is on top.

Another model for BLID is shown in FIG. 6. In this example a threading analysis was done using a murine Bcl-XL (PDB 1PQ0) as template and BLID SEQ ID NO: 2 as target. A favorable energy threading of −3.8 was obtained, again in line with the ones mentioned above. In this analysis more of the proposed interacting residues in the BLID frame are located on helices. A different overall arrangement is presented with a narrow space created by helices 3 and 4 in an antiparallel conformation, with the C-terminal of helix 2 making a re-enforcement of the entrance to the narrow canal made by helices 3 and 4 (Panel A).

A side view (Panel B) reveals the distribution of residues on the BLID frame with the hydrophobic residues at the bottom and the charged ones at the top of the channel created by the three helixes. The hydrophobic and charged sections of BLID are arranged to accommodate the amphipathic nature of a BH3 containing peptide like the one found in Bim. In addition a side view allows to see several residues from the hydrophobic section of BLID in very good alignment, they are: F19 and A22 (helix 2), M27 (just before helix 3) and A36 and A37 (loop between helix 3 and 4). In. very good alignment are also the following residues from the charge section: E44, E48 and H51, all of them on helix 4.

Figure 7:
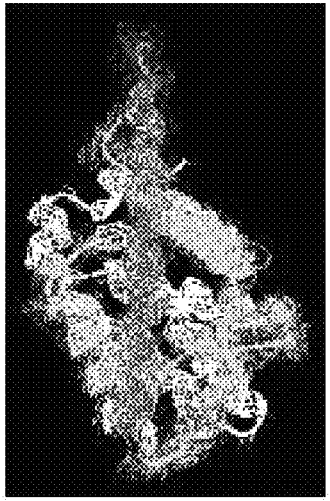
FIG. 7. Comparison of two BLID models obtained via homology modelling. A threading analysis was done using BLID SEQ ID NO: 2 as a target and two different crystal structures of anti-apoptotic proteins in complexes with their corresponding BH3 only pro-apoptotic molecules as templates. The experimental structures are Bcl-XL in complex with a BH3 peptide from Bim (PDB 1PQ1) and CED-9 in complex with a BH3 peptide from EGL-1 (PDB 1TY4). The threading energy was −3.6 and −2.5 respectively. Ribbons indicate structural features; dots indicate contact surfaces (Van der Waals radius). White is used for anti-apoptotic molecules, dark gray for pro-apoptotic molecules and light gray for BLID. Panels, from left to right, represent clockwise rotation of the models.
Figure 7:
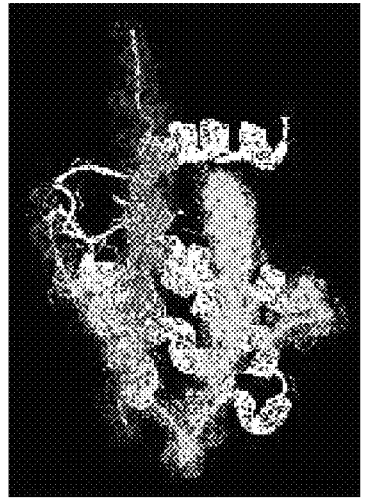
Figure 7:
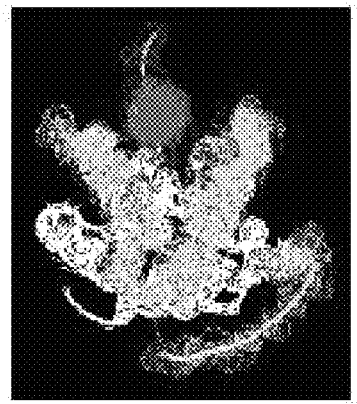
Figure 7:
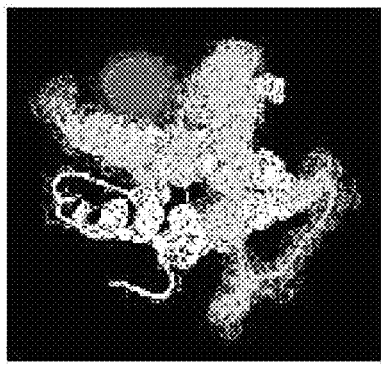

FIG. 7 shows A threading analysis was done using BLID SEQ ID NO: 2 as a target and two different crystal structures of anti-apoptotic proteins in complexes with their corresponding BH3 only pro-apoptotic molecules as templates. The experimental structures are Bcl-XL in complex with a BH3 peptide from Bim (PDB 1PQ1) and CED-9 in complex with a BH3 peptide from EGL-1 (PDB 1TY4). The threading energy was −3.6 and −2.5 respectively.

The finding of similar results in homology modelling exercises using three members of the Bcl-2 family of proteins (Bcl-XL, Bcl-w and CED9, a *c. elegans* Bcl-2 homologue) and BLID strengthens the case for the presence of a structural homolog in this newly defined LEDGF domain.

All of the above analysis suggests that there is a domain in LEDGF with a similar fold to members of the Bcl-2 family of proteins. This domain can be involved in a new type of protein-protein interaction with members of the Bcl-2 family of proteins. This constitutes a novel interaction for LEDGF, which previously has been regarded mainly as a transcriptional co-activator.

Because of the above mentioned potential novel interactions, BLID and its derivatives can be used as a way of modulating cell physiology; mainly apoptosis but also autophagy and necrosis. As a result, this invention can open new avenues in the fight against disease states like degenerative diseases, stroke, autoimmunity and cancer.

Example 2

Modulating Apoptosis in Mammalian Cells Using BLID and its Derivatives

BLID and several of its derivatives are realized. These molecules are assayed in two different ways to modulate apoptosis in mammalian cells. In the first way BLID and some of its derivatives are cloned into expression vectors like pcDNA1 (Invitrogen), etc and then transfected into mammalian cells (like CHO, Hela, Jurkat, HEK293 etc) and expressed. Stably transfected cell lines can also be established. Cells and controls are then challenged with apoptosis-inducing stimuli (actinomycin D, Staurosporine, etoposide etc) and phenotypic changes monitored via microscopy and subsequent assays like western blot for caspases, poly (ADP-ribose) polymerase (PARP) etc.

Figure 5:
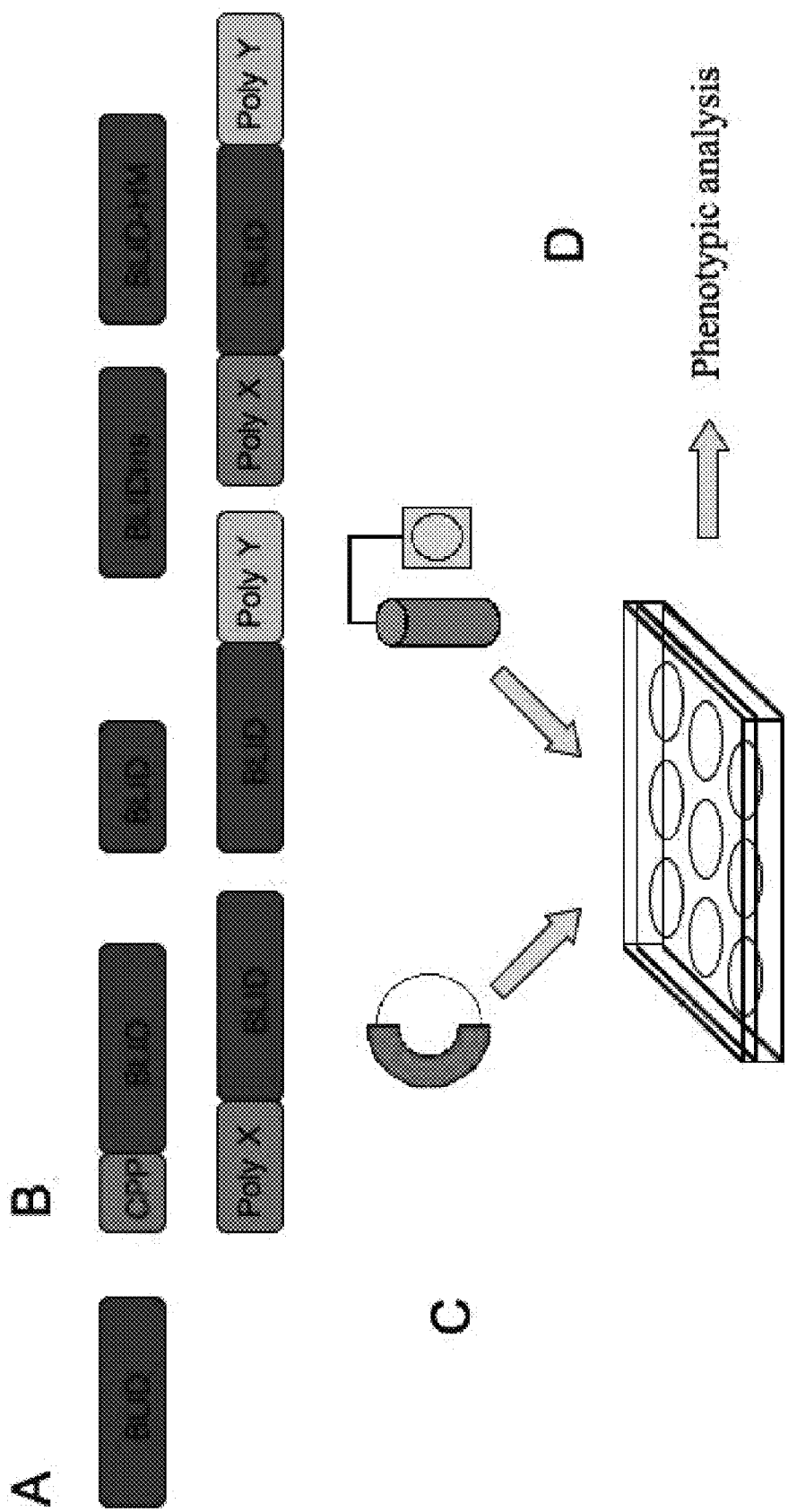
FIG. 5. Assaying phenotypic effects on mammalian cells of BLID and its derivatives. Building blocks for molecules used in testing modulation effect of BLID on cell processes like apoptosis. A) BLID B) BLID derivatives: BLID linked to a Cell Penetrating Peptide molecule, shorter versions of BLID, BLIDIns (BLID with a small aminoacidic insertion), BLID-HM (BLID with mutations on some modeled helices); PolyX, a heterologous polypeptide linked to BLID, for example GST (Glutathione-S-Transferase); PolyY, another heterologous polypeptide linked to BLID for example EGFP (Enhanced Green Fluorescent Protein). Building blocks can also be alternatively engineered in N or C terminal positions to the original design. C) The molecules are either cloned on expression vectors transfected and expressed on mammalian cells (left) or expressed on heterologous systems, purified and then added (right) to mammalian cells plated on 16, 96, etc well plates. D) Plates are analyzed for phenotypic changes.

The second way uses already purified BLID and derivatives, adding them to mammalian cells instead of expressing them in the target cells. FIG. 5 shows both approaches for assessing BLID. Different variants of BLID and its derivatives (expressed on mammalian cells or as purified polypeptides) are added to cells (with or without helpers like lipofectamine etc) or microinjected. In FIG. 5 several BLID and derivatives are realized. Cells are challenged with apoptosis-inducing agents, and then microscopy and subsequent assays are conducted to determine phenotypic and other molecular changes.

In FIG. 5 BLID variants are sequences from SEQ ID NOs: 1 to 24. Derivatives are created by modifying BLID in different ways: a) using shorter versions of BLID, for instance sequence 7, b) engineering short aminoacidic insertion into BLID (BLIDIns variant), c) designing mutations into predicted helical regions (BLID-HM), d) heterologous polypeptides cloned as fusion proteins to BLID or the above-mentioned variants. Examples of these polypeptides are EGFP and GST, e) Depending on delivery route, all of the above mentioned combinations could also be combined with Cell Penetrating Peptides (CPP). All of these building blocks can be also alternatively engineered in N or C terminal positions to the original design Cell Penetrating Peptides (CPP) are intended to help translocate BLID to the cell from the culture medium. Examples of these are: TAT, penetratin, transportan and polyarginines and polylysines of different lengths, typically around 9 residues long (Herce and Garcia, 2007).

Linkers used are aminoacids or chemical groups. Examples of aminoacids used for linkers are Glycine and Serine, with variable length, for instance between 3-15 residues. A preferred length would be between 3-5 residues long. Chemical groups used as linkers can be for instance thioesters.

Depending on the particular composition of an engineered molecule it can be produced entirely using recombinant technology, like in the example of a CPP-BLID molecule in which the CPP is cloned in frame C-terminal of BLID with a $Gly_3$-Ser linker in between them. In another variant, building blocks are produced individually via recombinant technology or chemically synthesized and then chemically linked. Alternatively, a whole variant molecule is made via chemical synthesis.

Cell lines which are used in particular disease models, can also be tested with BLID and its derivatives. Examples of those are N27 cells (mesencephalic dopaminergic neuronal cell line) used in Parkinson's disease studies (Carvour, 2008) and human retinal pigment epithelium (RPE) cells, which are used in Age-related macular degeneration (ARMD) studies (Jiang, 2005).

Example 3

In Vivo Assay for BLID Activity

HEK 293 or HeLa cells are seeded at ~$10^6$ cells per 15 cm dish. 72 hours later cells are transfected with pcDNA3.1 or pCruzHA vectors containing one of the following constructs: BLID sequences SEQ ID NO: 2, SEQ ID NO: 8, SEQ ID NO: 11 and SEQ ID NO: 17, BLID sequences SEQ ID NO: 2, SEQ ID NO: 8, SEQ ID NO: 11 and SEQ ID NO: 17 with a N-terminal fusion of GST, LEDGF/p52 and LEDGF/p75. Fugene 6 (Roche Diagnostics) or Lipofectamine 2000 (GIBCO BRLTechnologies Inc.) are used for the transfections. In addition controls of mock transfection and individual plasmids are used. 24-48 hours later apoptosis is induced by adding to the cells staurosporine (1 uM, or 250 nM) for 1.5, 3, 6, 12 and 24 h. Afterwards, cells are analyzed for apoptosis.

Microscopy: Cells are first analyzed by morphological changes, cell detachment, cells shrinkage etc using an inverted microscope (like an Olympus IX70 Microscope) equipped with Hoffman modulation contrast. Cells are counterstained with Hoechst 33342 and visualized directly using a 60× water immersion objective under an epifluorescence an Olympus BX50 (Scientific Instruments) microscope equipped with a digital camera system (digital SPOT camera system (Diagnostic Instruments)). Nuclei of cells that exhibited marked chromatin condensation, margination, or fragmentation are counted as apoptotic. Approximately 200 nuclei distributed in >10 different fields are counted in at least three independent double-blind experiments. Cells are selected for counting of apoptotic nuclei by their expression of BLID variants and BLID containing polypeptide using their corresponding tagged molecules; in the case of pCruzHA-based constructs, by an anti-HA antibody (rat monoclonal horseradish peroxidase (HRP)-conjugated anti-HA antibody (Roche Diagnostics)

When pCruzHA plasmids are used for transfection, cells are seeded on coverslips and fixed for 15 min at room temperature with 3.7% paraformaldehyde and permeabilized in PBS-0.2% Triton X-100 for 5 min. Coverslips are then incubated with rabbit anti-HA antibody for 2 h. Following three washes with PBS, cells are incubated with Alexa 488 goat anti-rabbit for 1 h, washed with PBS, mounted on glass slide with Vectashield Mounting Medium containing 4',6-diamidino-2-phenylindole, and examined under a fluorescence microscope. Localization of HA-tagged polypeptides as well as nuclear condensation is determined.

Cellular caspase activity: Activity in transfected and untreated cells is determined by cleavage of the fluorogenic substrate DEVD-AMC and expressed in relative fluorescence units (RFU), from which the value of the untreated control is subtracted.

Cells are seeded in black, clear-bottomed 96-well plates ($10^4$ cells per well). After 1.5, 3, 6, 12 and 24 h of subjecting cells to apoptotic stimuli, cells are incubated with 50 µl of 3× caspase buffer [150 mM Hepes pH 7.4, 450 mM sodium chloride, 150 mM potassium chloride, 30 mM magnesium chloride, 1.2 mM ethylene glycol-bis(2-aminoethylether)-N, N,N',N'-tetraacetic acid (EGTA), 30% sucrose, 10% CHAPS, and 1.5% NP-40], 30 mM dithiothreitol (DTT), 3 mM phenylmethanesulphonylfluoride (PMSF), and 75 µM of the fluorogenic peptide substrates Ac-DEVD-AMC (caspase-3/7) or Ac-VDVAD-AMC (caspase-2) for 2 h at 37° C., followed by incubation at room temperature for 12 h. TRAIL/actinomycin D treatment is used as a control for caspase-3/7 activation, whereas STS is used as a control for caspase-2 activation. Absorbance is then read in a Microplate Fluorescent Reader (like the FLX800 (Bio-tek Instruments)) at excitation of 360 nm and emission of 460 nm. Fold activity is determined by normalizing to one the absorbance values for untreated cells.

Cell survival is determined using the standard 3-(4,5-dimethylthiazol-2-yl)-2,5-diphenyl tetrazolium bromide (MTT) assay (Sigma-Aldrich). As an alternative, second-generation tetrazolium derivatives (e.g., 3-(4,5-dimethylthiazol-2-yl)-5-(3-carboxymethoxyphenyl)-2-(4-sulfophenyl)-2H-tetrazolium (MTS) or 4-[3-(4-iodophenyl)-2-(4-nitrophenyl)-2H-5-tetrazolio]-1,3-benzene disulfonate (WST-1)) can be used.

Cells are seeded in 96-well plates ($10^4$ cells per well), after 1.5, 3, 6, 12 and 24 h of subjecting cells to apoptotic stimuli they are washed with phosphate buffered saline (PBS), and fixed in 4% paraformaldehyde for 1 h at 4° C. Cells are then washed three times with distilled water, and Accustain Crystal Violet solution (Sigma-Aldrich) (1:4) is added to each well followed by incubation for 20 minutes at room temperature. Plates are washed with distilled water to remove excess dye and then dried at room temperature. Acetic acid (10% v/v) is added to each well for 10 minutes and absorbance is measured at 570 nanometers (nm) using a microplate reader (like the µQuant (Bio-tek Instruments)).

Cell viability can be also determined using a modified (3-(4,5-dimethylthiazol-2-yl)-2,5-diphenyltetrazolium bromide (MTT) assay (Sigma-Aldrich, St. Louis, Mo.). Briefly, cells are seeded in 96-well plates ($10^4$ cells per well) and then after 1.5, 3, 6, 12 and 24 h of subjecting the cells to apoptotic stimuli MTT is added to each well (final concentration, 1 mg/ml) and plates are incubated in a 5% CO2 incubator at 37° C. for 1 h. Plates are centrifuged at 2,000 rpm for 30 minutes. Supernatants are discarded and 150 µl of dimethyl sulfoxide (DMSO), are added to each well. Absorbance is measured at 450 nm.

Experimental alternatives to this example can be found below:

Other alternative cells to be used are: Jurkat, Normal human epidermal keratinocytes (NHEK), HepG2, HCT116, PC3 and mouse LensEpithelium Cells (LEC). Alternative methods of inducing apoptosis are subjecting the cells to actinomycin D, cisplatin (50 uM), or oligomycine (5 uM) plus carbonyl cyanide p-trifluoromethoxyphenylhydrazone (FCCP) (1 uM), anti-CD-95 (4 ug ml) plus CHX (cycloheximide) (2 ug/ml), exposing cells to 100 to 500 J/m² UV radiation, 200 mJ/cm² UV-C and 100 uM etoposide.

In this example the overexpression of BLID reduces or abolishes the apoptotic effect produced by the apoptotic stimuli therefore acting as an anti-apoptotic molecule and promoting cell survival. This effect of BLID constitutes one of the main avenues for drug development based on this novel protein-protein interaction domain.

Example 4

BLID Polypeptide Purification

BLID SEQ ID NOs: 1, 2, and 3 are amplified by PCR from a plasmid derived from plasmid GST-K-p52 (Ge, 1998) using primers designed using the DNA SEQ ID NO: 26. Additionally oligonucleotides encoding for a CPP (TAT-domain) are ligated to the amplified PCR fragments. The resulting sequences encode for a TAT-BLID fused polypeptide. Amplified PCR fragments are sub-cloned into cloning vectors (pBluescritp KS+ (Stratagene)), and verified by sequencing, The constructs are then cloned into pGEX plasmid (pGEX, Amersham, N.J.).

Clones are verified by sequencing. Vectors are transformed into E. coli and expressed. For protein expression E. coli Rosetta (pLysS) cells (Novagen, Madison, Wis.) are used, these are BL21 derivative designated to enhance the expression of eukaryotic proteins containing codons rarely used in E. coli.

Starter cultures of 5 ml Luria-Bertani (LB) medium containing 100 mg/ml ampicillin are inoculated, with a BL21 recombinant clone. The cultures are grown overnight at 250 rpm and 37° C. One milliliter of the overnight culture is added to 100 ml LB medium supplemented with 100 mg/ml ampicillin and further incubated at 37° C. up to an OD600 of 0.5. Culture is induced with IPTG at concentrations of 0.5 and 1 mM at an OD600 of 0.5, and at temperatures of 25° C. and 37° C. until reaching an OD of 2 at 600 nm.

Cells from induced and un-induced cultures are harvested by centrifugation (4000 g, 25 min, 4° C.) followed by two washing steps with buffer A (10 mM Na2HPO4, 2 mM KH2PO4, 150 mM NaCl, 2.5 mM KCl, pH 7.5) at 4000 g for 25 min, and stored at −80° C. until use. Protein extraction is performed by resuspending the cell pellet in one-fifth of the original culture volume of buffer B (10 mM Na2HPO4, 2 mM KH2PO4, 150 mM NaCl, 2.5 mM KCl, pH 7.5 and 1% Triton X-100). The cells are disrupted by sonication (5 20-sec bursts). The supernatant is collected by centrifugation at 4° C. for 30 min at 13 000 rpm. Both pellets and supernatants are stored at 4° C.

The supernatant containing the soluble GST-BLID and GST-TAT-BLID recombinant proteins are loaded on a GSTrap FF affinity column (1 ml; Amersham Biosciences) pre-equilibrated with buffer A (10 mM Na2HPO4, 2 mM KH2PO4, 150 mM NaCl, 2.5 mM KCl, pH 7.5) at a flow rate of 1 ml/min at room temperature. Washes are performed until baseline at 280 nm is reached. GST-BLID and GST-TAT-BLID elution are done by using five column volumes of elution buffer (50 mM Tris-HCl, 10 mM reduced glutathione, pH 8.0) at a 0.5 ml/min flow rate. The eluted fractions containing the GST-BLID and GST-TAT-BLID recombinant proteins are pooled. The purification steps and affinity chromatographic profiles are analyzed by Coomassie Blue-stained SDS-PAGE gels and by western blot analysis using anti-LEDGF antibody (BD Biosciences).

Afterwards, 20 units of thrombin solution are added per 100 mg of eluted fusion protein and incubated at room temperature for 18 h. Finally, the digestion reaction mix is loaded on a size-exclusion Sephacryl S-100 26/60 High Resolution column (Amersham-Biosciences) equilibrated with 200 mM NaCl, 50 mM Tris-HCl, pH 8.0, and the cleaved BLID and TAT-BLID peaks are eluted. The chromatographic profile is evaluated by Coomassie Blue, imidazole-stained SDS-PAGE gels and western blot. The purified polypeptides are stored at 4° C. and at −20° C. until further use.

Example 5

Cell Penetrating Peptides (CPP) also known as Protein Transduction Domain (PTD) can also be used to introduce BLID and derivatives into mammalian cells. CPP-BLID constructs are produced via two different technologies: recombinant techniques and chemical synthesis.

An example of a CPP-BLID (CPP-BLID-22) construct is one that comprises the first 19 residues of CPP (de Coupade 2005) and SEQ ID NO: 2

Purified polypeptides from Example 4 and a synthetic CPP-BLID-22 are used in this assay.

HeLa cells are maintained in DMEM (Dulbecco's modified Eagle's medium) supplemented with 10% (v/v) FCS (fetal calf serum), 2 mM L-glutamine and 1 mM sodium pyruvate. Cells are seeded and proteins are added 24 hours later with cells at 60-80% confluence. About $2 \times 10^5$ cells/ml are incubated at 37° C. in 5% CO2 atmosphere in complete culture medium with 2, 10, 25 and 75 µg/ml of a CPP-BLID in the presence of 100 µM chloroquine for 2, 4 and 8 hours.

Afterwards at 1 hour, 4 hours, 12 hours, 24 hours and 48 hours intervals apoptosis is induced by adding to the cells staurosporine (1 uM, or 250 nM) for 1.5, 3, 6, 12 and 24 h. Afterwards, cells are analyzed for cell survival and apoptosis as described in Example 3.

In this example the overexpression of BLID reduces or abolishes the apoptotic effect produced by the apoptotic stimuli therefore acting as an anti-apoptotic molecule and promoting cell survival. This effect of BLID constitutes one of the main avenues for drug development based on this novel protein-protein interaction domain.

REFERENCES

Andrew H. Wyllie. "Where, O Death, Is Thy Sting?" A Brief Review of Apoptosis Biology. Mol Neurobiol (2010) 42:4-9

Akiyama et al. "Bim-targeted cancer therapy: A link between drug action and underlying molecular changes". Mol Cancer Ther. (2009) 8:3173-3180.

Aoyagi et al. "Vaccinia virus N1L protein resembles a B cell lymphoma-2 (Bcl-2) family protein". Protein Sci (2007) 16: 118-124.

Ashkenazi and Herbst. "To kill a tumor cell: the potential of proapoptotic receptor agonists". J. Clin. Invest. (2008) 118: 1979-1990

Botbol et al. "Chromatinized templates reveal the requirement for the LEDGF/p75 PWWP domain during HIV-1 integration in vitro". Nucleic Acids Research (2008) 36 (4): 1237-1246.

Broustas et al. "BRCC2, a novel BH3-like domain-containing protein, induces apoptosis in a caspase-dependent manner". J Biol Chem (2004) 279: 26780-26788.

Broustas et al. "The Proapoptotic Molecule BLID Interacts with Bcl-XL and Its Downregulation in Breast Cancer Correlates with Poor Disease-Free and Overall Survival". Clin Cancer Res (2010) 16:2939-2948.

Carvour et al. "Chronic low dose oxidative stress induces caspase-3 dependent PKCδ proteolytic activation and apoptosis in a cell culture model of dopaminergic neurodegeneration". Ann N Y Acad Sci. (2008) 1139: 197-205.

Cherepanov et al. "HIV-1 integrase forms stable tetramers and associates with LEDGFp75 protein in human cells". J. Biol. Chem. (2003) 278:372-381.

Conradt, Barbara. "Genetic control of programmed cell death during animal development". Annu Rev Genet. (2009) 43: 493-523.

Cooray et al. "Functional and structural studies of the vaccinia virus virulence factor N1 reveal a Bcl-2-like anti-apoptotic protein". J Gen Virol (2007) 88: 1656-1666.

Debyser, et al. "Integrase cofactor". U.S. Pat. No. 7,514,233

Debyser, et al. "Integrase cofactor". U.S. Pat. No. 8,008,470 de Coupade et al. "Novel human-derived cell-penetrating peptides for specific subcellular delivery of therapeutic biomolecules". Biochem. J. (2005) 390, 407-418.

Douglas A E, Corbett K D, Berger J M, McFadden G, Handel T M. "Structure of M11L: A myxoma virus structural homolog of the apoptosis inhibitor, Bcl-2". Protein Sci (2007) 16: 695-703.

Drag and Salvesen "Emerging principles in protease-based drug discovery" Nat Rev Drug Discov. (2010) 9 (9): 690-701.

Garcia-Rivera et al. "Implication of Serine Residues 271, 273, and 275 in the Human Immunodeficiency Virus Type 1 Cofactor Activity of Lens Epithelium-Derived Growth Factor p75". J Virol (2010) 84(2): 740-752.

Ge et al. "Isolation of cDNAs encoding novel transcription coactivators p52 and p75 reveals an alternate regulatory mechanism of transcriptional activation". The EMBO Journal (1998) 17 (22): 6723-6729.

Goldstein, et al. "Compositions and methods for diagnosing tumors using LEDGF/p75" U.S. Pat. No. 8,168,393

Graham et al "Vaccinia Virus Proteins A52 and B14 Share a Bcl-2-Like Fold but Have Evolved to Inhibit NF-kB rather than Apoptosis". PLoS Pathogens (2008) 4 (8): e1000128.

Hattori et al. "Insights Into Sepsis Therapeutic Design Based on the Apoptotic Death Pathway" Journal of Pharmacological Sciences (2010) 114: 354-365

Hendrix et al. "The transcriptional co-activator LEDGF/p75 displays a dynamic scan-and-lock mechanism for chromatin tethering". Nucleic Acids Research (2011) 39 (4): 1310-1325.

Herce and Garcia. "Cell Penetrating Peptides: How Do They Do It?". J Biol Phys (2007) 33:345-356

Jiang et al. "Oxidant-Induced Apoptosis in Human Retinal Pigment Epithelial Cells: Dependence on Extracellular Redox State". Invest Ophthalmol Vis Sci. (2005) 46: 1054-1061.

Kasid et al. "Gene BRCC-2 and diagnostic and therapeutic uses thereof". U.S. Pat. No. 7,253,272.

Kvansakul et al. "Vaccinia virus anti-apoptotic F1L is a novel Bcl-2-like domain-swapped dimer that binds a highly selective subset of BH3-containing death ligands" Cell Death and Differentiation (2008) 15, 1564-1571

Leibowitz and Yu. "Mitochondrial signaling in cell death via the Bcl-2 family". Cancer Biol Ther (2010) 9(6): 417-422.

Llano et al. "Identification and Characterization of the Chromatin-binding Domains of the HIV-1 Integrase Interactor LEDGF/p75". J. Mol. Biol. (2006) 360, 760-773.

Lomonosova and Chinnadura. "From BH3-only proteins in apoptosis and beyond: an overview". Oncogene (2008) 27(Suppl 1): S2-19.

Matsui et al. "Lens Epithelium-Derived Growth Factor: Increased Survival and Decreased DNA Breakage of Human RPE Cells Induced by Oxidative Stress". Invest Ophthalmol Vis Sci. (2001) 42: 2935-2941.

Meehan et al. "LEDGF/p75 Proteins with Alternative Chromatin Tethers Are Functional HIV-1 Cofactors". PLoS Pathog (2009) 5(7): e1000522.

Nemec and Khaled. "Therapeutic Modulation of Apoptosis: Targeting the BCL-2 Family at the Interface of the Mitochondrial Membrane" Yonsei Med J (2008) 49(5): 689-697.

Sambrook et al., "Molecular Cloning: A Laboratory Manual" (2 ed.), Cold Spring Harbor Laboratory Press, Cold Spring Harbor, N.Y., USA (1989).

Sasi et al. "Regulated cell death pathways: New twists in modulation of BCL2 family function". Mol Cancer Ther (2009) 8:1421-1429.

Shinohara, et al. "Lens epithelial cell derived growth factor". U.S. Pat. No. 6,750,052

Shun et al. "Identification and Characterization of PWWP Domain Residues Critical for LEDGF/p75 Chromatin Binding and Human Immunodeficiency Virus Type 1 Infectivity". Journal of Virology (2008) 82 (23): 11555-11567

Singh et al. "Lens Epithelium-Derived Growth Factor: Increased Resistance to Thermal and Oxidative Stresses". Invest Ophthalmol Vis Sci. (1999) 40:1444-1451

Sinha and Levine. "The autophagy effector Beclin 1: a novel BH3-only protein". Oncogene (2008) 27(Suppl 1): S137-S148.

Sugiura et al. "LEDGF/DFS70, a Major Autoantigen of Atopic Dermatitis, Is a Component of Keratohyalin Granules". Journal of Investigative Dermatology (2007) 127: 75-80.

Sutherland et al. "Disruption of Ledgf/Psip1 Results in Perinatal Mortality and Homeotic Skeletal Transformations". Molecular and Cellular Biology (2006) 26 (19): 7201-7210

Tischner et al. "Bcl-2-regulated cell death signalling in the prevention of autoimmunity" Cell Death and Disease (2010) 1, e48

Vlahovicek et al. "CX, DPX and PRIDE: WWW servers for the analysis and comparison of protein 3D structures". Nucleic Acids Research, (2005) 33: W252-W254.

Volbracht et al. "Apoptosis in Caspase-inhibited Neurons". Molecular Medicine (2001) 7(1): 36-48.

The invention claimed is:

1. A method for attenuating apoptosis in a cell, said method comprising the step of applying into a cell an isolated polypeptide consisting of the amino acid sequence set forth in any one of SEQ ID NO: 1 through 24, or a fragment thereof, or expressing in a cell a nucleic acid encoding a polypeptide consisting of the amino acid sequence set forth in any one of SEQ ID NO: 1 through 24, or a fragment thereof, wherein said polypeptide or fragment thereof is capable of protein-protein interaction with Bcl-2 family proteins, wherein apoptosis is attenuated in said cell.

2. The method of claim 1, wherein the polypeptide is a chimeric polypeptide directly linked to a heterologous polypeptide selected from the group consisting of fluorescent proteins, glutathione-S-transferase, maltose binding protein, beta-galactosidase, inteins, streptavidin, His-tag, myc epitope, HA-tag, and FLAG.

3. The method of claim 1, wherein the polypeptide is a chimeric polypeptide linked through a heterologous consisting of any one of SEQ ID NO: 29 through 32 to a heterologous polypeptide selected from the group consisting of fluorescent proteins, glutathione-S-transferase, maltose binding protein, beta-galactosidase, inteins, streptavidin, His-tag, myc epitope, HA-tag, and FLAG.

4. The method of claim 1, wherein the polypeptide is a chimeric polypeptide directly linked to a heterologous cell penetrating peptide, and optionally to a heterologous polypeptide selected from the group consisting of fluorescent proteins, glutathione-S-transferase, maltose binding protein, beta-galactosidase, inteins, streptavidin, His-tag, myc, epitope, HA-tag, and FLAG.

5. The method of claim 1, wherein the polypeptide is a chimeric polypeptide directly linked through a heterologous linker consisting of any one of SEQ ID NO: 29 through 32 to a heterologous cell penetrating peptide, and wherein the chimeric polypeptide may optionally include a heterologous polypeptide selected from the group consisting of fluorescent proteins, glutathione-S-transferase, maltose binding protein, beta-galactosidase, inteins, streptavidin, His-tag, myc epitope, HA-tag, and FLAG, said heterologous polypeptide directly linked to the polypeptide or the cell penetrating peptide, or directly linked to the polypeptide or the cell penetrating peptide through the linker consisting of SEQ ID NO: 29 through 32.

6. The method of claim 1 where the polypeptide is applied to the cell by expressing it inside the cell using an expression or viral vector.

7. The method of claim 1, where the polypeptides are introduced into the cell using microinjection or lipofectamine.

8. The method of claim 1, said method further including the step of subjecting the cell to an apoptotic challenge by exposing it to an apoptotic inducing agent selected from the group consisting of staurosporine, etoposide, and UV irradiation.

9. The method of claim 8, said method further including determining cellular viability by a method selected from the group consisting of diphenyl tetrazolium bromide assay, second generation tetrazolium derivatives assays, and the presence of at least one apoptotic marker, said apoptotic marker selected from the group consisting of cellular caspase activity, cell detachment, cell shrinkage and chromatin condensation.

\* \* \* \* \*

SEQUENCE LISTING

```
<160> NUMBER OF SEQ ID NOS: 32

<210> SEQ ID NO 1
<211> LENGTH: 89
<212> TYPE: PRT
<213> ORGANISM: Homo sapiens

<400> SEQUENCE: 1

Arg Lys Glu Pro Asp Lys Lys Glu Gly Lys Glu Val Glu Ser Lys
1               5                   10                  15

Arg Lys Asn Leu Ala Lys Thr Gly Val Thr Ser Thr Ser Asp Ser Glu
            20                  25                  30

Glu Glu Gly Asp Asp Gln Glu Gly Glu Lys Lys Arg Lys Gly Gly Arg
        35                  40                  45

Asn Phe Gln Thr Ala His Arg Arg Asn Met Leu Lys Gly Gln His Glu
    50                  55                  60

Lys Glu Ala Ala Asp Arg Lys Arg Lys Gln Glu Glu Gln Met Glu Thr
65                  70                  75                  80

Glu His Gln Thr Thr Cys Asn Leu Gln
                85

<210> SEQ ID NO 2
<211> LENGTH: 71
<212> TYPE: PRT
<213> ORGANISM: Homo sapiens

<400> SEQUENCE: 2

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45
```

Ala Ala Asp Arg Lys Arg Lys Gln Glu Glu Gln Met Glu Thr Glu His
    50                  55                  60

Gln Thr Thr Cys Asn Leu Gln
65                  70

<210> SEQ ID NO 3
<211> LENGTH: 60
<212> TYPE: PRT
<213> ORGANISM: Homo sapiens

<400> SEQUENCE: 3

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45

Ala Ala Asp Arg Lys Arg Lys Gln Glu Glu Gln Met
    50                  55                  60

<210> SEQ ID NO 4
<211> LENGTH: 65
<212> TYPE: PRT
<213> ORGANISM: Homo sapiens

<400> SEQUENCE: 4

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45

Ala Ala Asp Arg Lys Arg Lys Gln Glu Glu Gln Met Glu Thr Glu His
    50                  55                  60

Gln
65

<210> SEQ ID NO 5
<211> LENGTH: 66
<212> TYPE: PRT
<213> ORGANISM: Homo sapiens

<400> SEQUENCE: 5

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45

Ala Ala Asp Arg Lys Arg Lys Gln Glu Glu Gln Met Glu Thr Glu His
    50                  55                  60

Gln Thr
65

<210> SEQ ID NO 6
<211> LENGTH: 58
<212> TYPE: PRT
<213> ORGANISM: Homo sapiens

<400> SEQUENCE: 6

Glu Glu Glu Gly Asp Asp Gln Glu Gly Glu Lys Lys Arg Lys Gly
1               5                   10                  15

Arg Asn Phe Gln Thr Ala His Arg Arg Asn Met Leu Lys Gly Gln His
            20                  25                  30

Glu Lys Glu Ala Ala Asp Arg Lys Arg Lys Gln Glu Gln Met Glu
        35                  40                  45

Thr Glu His Gln Thr Thr Cys Asn Leu Gln
    50                  55

<210> SEQ ID NO 7
<211> LENGTH: 71
<212> TYPE: PRT
<213> ORGANISM: Homo sapiens

<400> SEQUENCE: 7

Glu Ser Lys Arg Lys Asn Leu Ala Lys Thr Gly Val Thr Ser Thr Ser
1               5                   10                  15

Asp Ser Glu Glu Glu Gly Asp Asp Gln Glu Gly Glu Lys Lys Arg Lys
            20                  25                  30

Gly Gly Arg Asn Phe Gln Thr Ala His Arg Arg Asn Met Leu Lys Gly
        35                  40                  45

Gln His Glu Lys Glu Ala Ala Asp Arg Lys Arg Lys Gln Glu Glu Gln
    50                  55                  60

Met Glu Thr Glu His Gln Thr
65                  70

<210> SEQ ID NO 8
<211> LENGTH: 76
<212> TYPE: PRT
<213> ORGANISM: Homo sapiens

<400> SEQUENCE: 8

Gly Lys Lys Glu Val Glu Ser Lys Arg Lys Asn Leu Ala Lys Thr Gly
1               5                   10                  15

Val Thr Ser Thr Ser Asp Ser Glu Glu Glu Gly Asp Asp Gln Glu Gly
            20                  25                  30

Glu Lys Lys Arg Lys Gly Gly Arg Asn Phe Gln Thr Ala His Arg Arg
        35                  40                  45

Asn Met Leu Lys Gly Gln His Glu Lys Glu Ala Ala Asp Arg Lys Arg
    50                  55                  60

Lys Gln Glu Glu Gln Met Glu Thr Glu His Gln Thr
65                  70                  75

<210> SEQ ID NO 9
<211> LENGTH: 81
<212> TYPE: PRT
<213> ORGANISM: Homo sapiens

<400> SEQUENCE: 9

Pro Asp Lys Lys Glu Gly Lys Lys Glu Val Glu Ser Lys Arg Lys Asn
1               5                   10                  15

Leu Ala Lys Thr Gly Val Thr Ser Thr Ser Asp Ser Glu Glu Glu Gly
            20                  25                  30

Asp Asp Gln Glu Gly Glu Lys Lys Arg Lys Gly Gly Arg Asn Phe Gln
        35                  40                  45

Thr Ala His Arg Arg Asn Met Leu Lys Gly Gln His Glu Lys Glu Ala
    50                  55                  60

```
Ala Asp Arg Lys Arg Lys Gln Glu Glu Gln Met Glu Thr Glu His Gln
 65                  70                  75                  80

Thr

<210> SEQ ID NO 10
<211> LENGTH: 84
<212> TYPE: PRT
<213> ORGANISM: Homo sapiens

<400> SEQUENCE: 10

Arg Lys Glu Pro Asp Lys Lys Glu Gly Lys Lys Glu Val Glu Ser Lys
  1               5                  10                  15

Arg Lys Asn Leu Ala Lys Thr Gly Val Thr Ser Thr Ser Asp Ser Glu
             20                  25                  30

Glu Glu Gly Asp Asp Gln Glu Gly Leu Lys Arg Lys Gly Gly Arg
         35                  40                  45

Asn Phe Gln Thr Ala His Arg Arg Asn Met Leu Lys Gly Gln His Glu
     50                  55                  60

Lys Glu Ala Ala Asp Arg Lys Arg Lys Gln Glu Gln Met Glu Thr
 65                  70                  75                  80

Glu His Gln Thr

<210> SEQ ID NO 11
<211> LENGTH: 58
<212> TYPE: PRT
<213> ORGANISM: Homo sapiens

<400> SEQUENCE: 11

Ser Thr Ser Asp Ser Glu Glu Glu Gly Asp Asp Gln Glu Gly Glu Lys
  1               5                  10                  15

Lys Arg Lys Gly Gly Arg Asn Phe Gln Thr Ala His Arg Arg Asn Met
             20                  25                  30

Leu Lys Gly Gln His Glu Lys Glu Ala Ala Asp Arg Lys Arg Lys Gln
         35                  40                  45

Glu Glu Gln Met Glu Thr Glu His Gln Thr
     50                  55

<210> SEQ ID NO 12
<211> LENGTH: 89
<212> TYPE: PRT
<213> ORGANISM: Homo sapiens

<400> SEQUENCE: 12

Arg Lys Glu Pro Asp Lys Lys Glu Gly Lys Lys Glu Val Glu Ser Lys
  1               5                  10                  15

Arg Lys Asn Leu Ala Lys Thr Gly Val Thr Ser Thr Ser Asp Ser Glu
             20                  25                  30

Glu Glu Gly Asp Asp Gln Glu Gly Leu Lys Arg Lys Gly Gly Arg
         35                  40                  45

Asn Phe Gln Thr Ala His Arg Arg Asn Met Leu Lys Gly Gln His Glu
     50                  55                  60

Lys Glu Ala Ala Asp Arg Lys Arg Lys Gln Glu Gln Met Glu Thr
 65                  70                  75                  80

Glu Gln Gln Asn Lys Asp Glu Gly Lys
             85

<210> SEQ ID NO 13
<211> LENGTH: 71
```

<212> TYPE: PRT
<213> ORGANISM: Homo sapiens

<400> SEQUENCE: 13

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45

Ala Ala Asp Arg Lys Arg Lys Gln Glu Glu Gln Met Glu Thr Glu Gln
    50                  55                  60

Gln Asn Lys Asp Glu Gly Lys
65                  70

<210> SEQ ID NO 14
<211> LENGTH: 60
<212> TYPE: PRT
<213> ORGANISM: Homo sapiens

<400> SEQUENCE: 14

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45

Ala Ala Asp Arg Lys Arg Lys Gln Glu Glu Gln Met
    50                  55                  60

<210> SEQ ID NO 15
<211> LENGTH: 65
<212> TYPE: PRT
<213> ORGANISM: Homo sapiens

<400> SEQUENCE: 15

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45

Ala Ala Asp Arg Lys Arg Lys Gln Glu Glu Gln Met Glu Thr Glu Gln
    50                  55                  60

Gln
65

<210> SEQ ID NO 16
<211> LENGTH: 70
<212> TYPE: PRT
<213> ORGANISM: Homo sapiens

<400> SEQUENCE: 16

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45

Ala Ala Asp Arg Lys Arg Lys Gln Glu Glu Gln Met Glu Thr Glu Gln
    50                  55                  60

Gln Asn Lys Asp Glu Gly
65                  70

<210> SEQ ID NO 17
<211> LENGTH: 72
<212> TYPE: PRT
<213> ORGANISM: Homo sapiens

<400> SEQUENCE: 17

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45

Ala Ala Asp Arg Lys Arg Lys Gln Glu Glu Gln Met Glu Thr Glu Gln
    50                  55                  60

Gln Asn Lys Asp Glu Gly Lys Lys
65                  70

<210> SEQ ID NO 18
<211> LENGTH: 73
<212> TYPE: PRT
<213> ORGANISM: Homo sapiens

<400> SEQUENCE: 18

Asn Leu Ala Lys Thr Gly Val Thr Ser Thr Ser Asp Ser Glu Glu Glu
1               5                   10                  15

Gly Asp Asp Gln Glu Gly Glu Lys Lys Arg Lys Gly Gly Arg Asn Phe
            20                  25                  30

Gln Thr Ala His Arg Arg Asn Met Leu Lys Gly Gln His Glu Lys Glu
        35                  40                  45

Ala Ala Asp Arg Lys Arg Lys Gln Glu Glu Gln Met Glu Thr Glu Gln
    50                  55                  60

Gln Asn Lys Asp Glu Gly Lys Lys Pro
65                  70

<210> SEQ ID NO 19
<211> LENGTH: 58
<212> TYPE: PRT
<213> ORGANISM: Homo sapiens

<400> SEQUENCE: 19

Glu Glu Glu Gly Asp Asp Gln Glu Gly Glu Lys Lys Arg Lys Gly Gly
1               5                   10                  15

Arg Asn Phe Gln Thr Ala His Arg Arg Asn Met Leu Lys Gly Gln His
            20                  25                  30

Glu Lys Glu Ala Ala Asp Arg Lys Arg Lys Gln Glu Glu Gln Met Glu
        35                  40                  45

Thr Glu Gln Gln Asn Lys Asp Glu Gly Lys
    50                  55

<210> SEQ ID NO 20
<211> LENGTH: 31
<212> TYPE: PRT
<213> ORGANISM: Homo sapiens -continued

```
<400> SEQUENCE: 20

Gly Glu Lys Lys Arg Lys Gly Gly Arg Asn Phe Gln Thr Ala His Arg
1               5                   10                  15

Arg Asn Met Leu Lys Gly Gln His Glu Lys Glu Ala Ala Asp Arg
            20                  25                  30

<210> SEQ ID NO 21
<211> LENGTH: 77
<212> TYPE: PRT
<213> ORGANISM: Homo sapiens

<400> SEQUENCE: 21

Glu Ser Lys Arg Lys Asn Leu Ala Lys Thr Gly Val Thr Ser Thr Ser
1               5                   10                  15

Asp Ser Glu Glu Glu Gly Asp Asp Gln Glu Gly Glu Lys Lys Arg Lys
            20                  25                  30

Gly Gly Arg Asn Phe Gln Thr Ala His Arg Arg Asn Met Leu Lys Gly
        35                  40                  45

Gln His Glu Lys Glu Ala Ala Asp Arg Lys Arg Lys Gln Glu Glu Gln
    50                  55                  60

Met Glu Thr Glu Gln Gln Asn Lys Asp Glu Gly Lys Lys
65                  70                  75

<210> SEQ ID NO 22
<211> LENGTH: 82
<212> TYPE: PRT
<213> ORGANISM: Homo sapiens

<400> SEQUENCE: 22

Gly Lys Lys Glu Val Glu Ser Lys Arg Lys Asn Leu Ala Lys Thr Gly
1               5                   10                  15

Val Thr Ser Thr Ser Asp Ser Glu Glu Glu Gly Asp Asp Gln Glu Gly
            20                  25                  30

Glu Lys Lys Arg Lys Gly Gly Arg Asn Phe Gln Thr Ala His Arg Arg
        35                  40                  45

Asn Met Leu Lys Gly Gln His Glu Lys Glu Ala Ala Asp Arg Lys Arg
    50                  55                  60

Lys Gln Glu Glu Gln Met Glu Thr Glu Gln Gln Asn Lys Asp Glu Gly
65                  70                  75                  80

Lys Lys

<210> SEQ ID NO 23
<211> LENGTH: 87
<212> TYPE: PRT
<213> ORGANISM: Homo sapiens

<400> SEQUENCE: 23

Pro Asp Lys Lys Glu Gly Lys Lys Glu Val Glu Ser Lys Arg Lys Asn
1               5                   10                  15

Leu Ala Lys Thr Gly Val Thr Ser Thr Ser Asp Ser Glu Glu Glu Gly
            20                  25                  30

Asp Asp Gln Glu Gly Lys Lys Arg Lys Gly Gly Arg Asn Phe Gln
        35                  40                  45

Thr Ala His Arg Arg Asn Met Leu Lys Gly Gln His Glu Lys Glu Ala
    50                  55                  60

Ala Asp Arg Lys Arg Lys Gln Glu Glu Gln Met Glu Thr Glu Gln Gln
65                  70                  75                  80
```

```
Asn Lys Asp Glu Gly Lys Lys
            85
```

<210> SEQ ID NO 24
<211> LENGTH: 90
<212> TYPE: PRT
<213> ORGANISM: Homo sapiens

<400> SEQUENCE: 24

```
Arg Lys Glu Pro Asp Lys Lys Glu Gly Lys Lys Glu Val Ser Lys
 1               5                  10                  15

Arg Lys Asn Leu Ala Lys Thr Gly Val Thr Ser Thr Ser Asp Ser Glu
                20                  25                  30

Glu Glu Gly Asp Asp Gln Gly Glu Lys Lys Arg Lys Gly Gly Arg
            35                  40                  45

Asn Phe Gln Thr Ala His Arg Arg Asn Met Leu Lys Gly Gln His Glu
    50                  55                  60

Lys Glu Ala Ala Asp Arg Lys Arg Lys Gln Glu Glu Gln Met Glu Thr
65                  70                  75                  80

Glu Gln Gln Asn Lys Asp Glu Gly Lys Lys
                85                  90
```

<210> SEQ ID NO 25

<400> SEQUENCE: 25

000

<210> SEQ ID NO 26
<211> LENGTH: 267
<212> TYPE: DNA
<213> ORGANISM: Homo sapiens

<400> SEQUENCE: 26

```
agaaaagagc cggataaaaa agaggggaag aaagaagttg aatcaaaaag gaaaaattta      60
gctaaaacag gggttacttc aacctccgat tctgaagaag aaggagatga tcaagaaggt     120
gaaaagaaga gaaaaggtgg gaggaacttt cagactgctc acagaaggaa tatgctgaaa     180
ggccaacatg agaaagaagc agcagatcga aaacgcaagc aagaggaaca aatggaaact     240
gagcaccaaa caacatgtaa tctacag                                         267
```

<210> SEQ ID NO 27
<211> LENGTH: 267
<212> TYPE: DNA
<213> ORGANISM: Homo sapiens

<400> SEQUENCE: 27

```
agaaaagagc cggataaaaa agaggggaag aaagaagttg aatcaaaaag gaaaaattta      60
gctaaaacag gggttacttc aacctccgat tctgaagaag aaggagatga tcaagaaggt     120
gaaaagaaga gaaaaggtgg gaggaacttt cagactgctc acagaaggaa tatgctgaaa     180
ggccaacatg agaaagaagc agcagatcga aaacgcaagc aagaggaaca aatggaaact     240
gagcagcaga ataaagatga aggaaag                                         267
```

<210> SEQ ID NO 28

<400> SEQUENCE: 28

000

```
-continued

<210> SEQ ID NO 29
<211> LENGTH: 4
<212> TYPE: PRT
<213> ORGANISM: Artificial Sequence
<220> FEATURE:
<223> OTHER INFORMATION: Synthetic Construct

<400> SEQUENCE: 29

Gly Ser Gly Ser
1

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Gly Ser Gly Gly Ser Gly Ser
1               5

<210> SEQ ID NO 31
<211> LENGTH: 11
<212> TYPE: PRT
<213> ORGANISM: Artificial Sequence
<220> FEATURE:
<223> OTHER INFORMATION: Synthetic Construct

<400> SEQUENCE: 31

Gly Ser Gly Gly Ser Gly Ser Gly Gly Gly Ser
1               5                   10

<210> SEQ ID NO 32
<211> LENGTH: 4
<212> TYPE: PRT
<213> ORGANISM: Artificial Sequence
<220> FEATURE:
<223> OTHER INFORMATION: Synthetic Construct

<400> SEQUENCE: 32

Gly Gly Gly Ser
1
```